(12) United States Patent
Woodbury et al.

(10) Patent No.: US 7,193,706 B2
(45) Date of Patent: Mar. 20, 2007

(54) COMPUTER INTERFACED SCANNING FLUORESCENCE LIFETIME MICROSCOPE APPLIED TO DIRECTED EVOLUTION

(75) Inventors: Neal W. T. Woodbury, Tempe, AZ (US); Benjamin P. Bowen, Tempe, AZ (US); Allan Scruggs, Tempe, AZ (US)

(73) Assignee: Arizona Board of Regents, Acting on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 10/343,412

(22) PCT Filed: Aug. 2, 2001

(86) PCT No.: PCT/US01/24365

§ 371 (c)(1),
(2), (4) Date: Jan. 28, 2003

(87) PCT Pub. No.: WO02/19594

PCT Pub. Date: Mar. 7, 2002

(65) Prior Publication Data

US 2003/0148393 A1    Aug. 7, 2003

Related U.S. Application Data

(60) Provisional application No. 60/222,691, filed on Aug. 2, 2000.

(51) Int. Cl.
  *G01J 3/30* (2006.01)
(52) U.S. Cl. ............ 356/317; 356/210; 435/40.2; 435/85.5; 435/173.1; 435/173.4; 514/183; 514/31; 522/25; 522/26

(58) Field of Classification Search ........... 356/317, 356/210; 435/85.5, 173.1, 7.2, 173.4, 40.2; 514/183, 31, 410, 561, 152, 192; 424/85.5, 424/577, 600; 604/20, 21; 607/88, 89; 522/25, 522/26, 2
See application file for complete search history.

(56) References Cited

U.S. PATENT DOCUMENTS 4,629,687 A * 12/1986 Schindler et al. .............. 435/4

(Continued)

FOREIGN PATENT DOCUMENTS

WO      WO 00/79241 A2    12/2000

OTHER PUBLICATIONS

Morgan et al, Comparison of photodynamic targets in a carcinoma cell line and its mitochondrial DNA-deficient derivative, Mar. 2000, Photochem Photobio, 71(6): 747-757.*

(Continued)

*Primary Examiner*—Long V. Le
*Assistant Examiner*—N Yang
(74) *Attorney, Agent, or Firm*—Needle & Rosenberg, P.C.

(57) ABSTRACT

This invention provides a method for screening large numbers of individual cells or colonies of cells using scanning microscopy coupled with fluorescence lifetime measurement and analysis, using time-correlated single photon counting. This invention further provides an automated method for selecting cells that exhibit desired characteristics. The method uses the scanning microscope system to focus a laser beam onto a surface upon which cells are immobilized on the timescale of the procedure. The cells that are illuminated in this way are killed or their growth is inhibited. The focused laser beam is scanned across the surface and turned on and off during the scanning process such that only non-irradiated cells survive, resulting in a patterned cell growth This invention further provides a computer-controlled projection device, such as a micromirror array or a liquid crystal display system, which is sued to project an image onto the cells.

14 Claims, 9 Drawing Sheets

U.S. PATENT DOCUMENTS

| | | |
|---|---|---|
| 4,791,310 A | 12/1988 | Honig et al. |
| 5,071,416 A | 12/1991 | Heller et al. |
| 5,089,384 A | 2/1992 | Hale |
| 5,095,030 A | 3/1992 | Levy et al. |
| 5,548,661 A | 8/1996 | Price et al. |
| 5,635,402 A | 6/1997 | Alfano et al. |
| 5,670,113 A | 9/1997 | Akong et al. |
| 5,721,613 A | 2/1998 | Linowski et al. |
| 5,770,619 A * | 6/1998 | Richter et al. .............. 514/410 |
| 5,955,490 A | 9/1999 | Kennedy et al. |
| 5,989,835 A | 11/1999 | Dunlay et al. |
| 6,040,139 A | 3/2000 | Bova |
| 6,042,603 A | 3/2000 | Fisher et al. |
| 6,143,535 A | 11/2000 | Palsson |
| 6,149,671 A * | 11/2000 | Nordquist et al. ............ 607/89 |
| 6,248,734 B1 | 6/2001 | Meadows et al. |
| 6,290,712 B1 * | 9/2001 | Nordquist et al. ............ 607/88 |
| 6,545,758 B1 * | 4/2003 | Sandstrom .................. 356/317 |
| 6,567,163 B1 * | 5/2003 | Sandstrom .................. 356/317 |
| 6,642,018 B1 * | 11/2003 | Koller et al. .............. 435/40.5 |

OTHER PUBLICATIONS

Keskinova, E. "Effects of High-Intensity UV Radiation on Isolated and DNA-Intercalated Ethidium Bromide" Fizika A 7 (1998) 1, 17-26.

* cited by examiner

Figure 1. The general scheme for directed evolution.

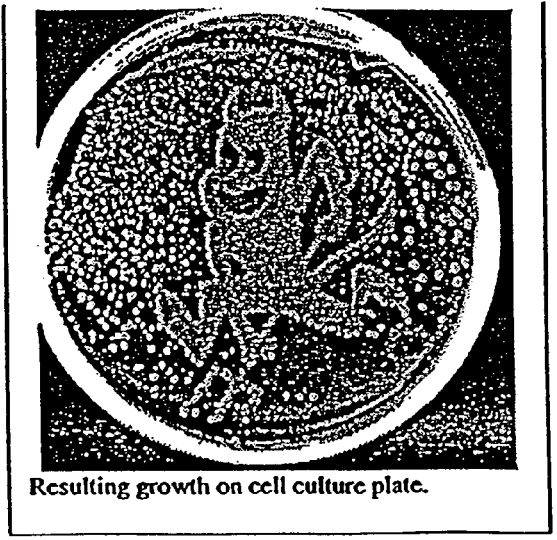
FIG. 9

COMPUTER INTERFACED SCANNING FLUORESCENCE LIFETIME MICROSCOPE APPLIED TO DIRECTED EVOLUTION

CROSS-REFERENCE TO RELATED APPLICATIONS

This application claims priority of International Application No. PCT/US01/24365, entitled SCANNING FLUORESCENCE LIFETIME MICROSCOPE: DIRECTED EVOLUTION, filed Aug. 2, 2001, which in turn claims priority to U.S. Provisional Application No. 60/222,691, filed Aug. 2, 2000, entitled COMPUTER INTERFACED SCANNING FLUORESCENCE LIFETIME MICROSCOPE APPLIED TO DIRECTED EVOLUTION METHODOLOGIES AND METHODS FOR LIGHT-MEDIATED PATTERNING IN CELL SELECTION, which are hereby incorporated by reference in their entirety.

FIELD OF THE INVENTION

The present invention relates generally to an apparatus and methods for rapidly and automatically screening and selecting cells exhibiting desirable physical traits and more specifically to a computer interfaced scanning fluorescence microscope applied to directed evolution methodologies and methods for light-mediated patterning in cell selection.

BACKGROUND OF THE INVENTION

Directed evolution is a process wherein the sequence of a gene is varied randomly by any of a number of methods, generating a library of mutated genes. These mutated genes are expressed and the functions of those gene products are assayed. A selection procedure is then applied to select those cells containing genes that express products-with desirable functions. These cells, and their genes, are then selectively amplified, and the mutagenesis, screening and selection process is repeated until gene products with the most desirable functions are obtained.

The general scheme for directed evolution is shown in FIG. 1. First, variation is introduced into the gene in question by some type of random mutagenesis and a library of sequences is introduced into an organism (typically *Escherichia coli*) for expression of the altered proteins. Next, this population of bacteria is screened for the desired activity and individual colonies are selected. Finally, these selected bacteria are grown up (amplification of the selected genetic variants) and the plasmids expressing proteins with the most desirable functional traits are isolated. These then are used as heterogeneous templates for further random mutagenesis and reintroduced into the bacterium for another round of screening and amplification. This cycle is continued until the desired functional characteristics are achieved.

Directed evolution has been successfully used to generate new molecules with altered physical characteristics. For example, Doi et al. modified green fluorescent protein (GFP) to include a binding site for the TEM1-lactamase inhibitor and then used directed evolution methods to produce a protein molecule whose fluorescent properties changed upon binding the target molecule. N. Doi and H. Yanagawa (1999) "Design of generic biosensors based on green fluorescent proteins with allosteric sites by directed evolution," *FEBS Letters* 453, 305–307). Directed evolution methodologies involving fluorescent proteins are particularly useful as fluorescence lends itself to sensitive and relatively easy, albeit slow, visual measurement.

GFP is one of a few different proteins that, in the absence of any externally supplied cofactor, fluoresce strongly in the visible region of the spectrum. Two of these proteins, GFP and a related red fluorescing protein (RFP) from reef corals, are commercially available in the form of expressible plasmids. Tsien, R. Y. (1998) "The Green Fluorescent Protein," *Annu. Rev. Biochem.* 67:509–544; Matz, V., et al. (1999) "Fluorescent proteins from nonbioluminescent Anthozoa species," *Nature Biotechnology* 17: 1969–1973. Functional transgenic expression of these fluorescent proteins is nearly universal in both eukaryotes and prokaryotes. Both the green and red fluorescing proteins have similar structural features, involving a beta-can fold structure enclosing a chromophore that is made via a reaction between 3 consecutive amino acids, serine, tyrosine and glycine. The quantum yield of fluorescence from the green fluorescent protein is near unity, while that from the red protein is apparently lower. Proteins with a variety of intermediate wavelengths have also been characterized.

Most of the directed evolution studies performed to date have utilized visual, qualitative screening of colonies on plates followed by manual selection of colonies that have enhanced activity in the protein of interest. Selection of cells may be based on a number of criteria, including color, morphology, size and fluorescence, depending on the protein of interest and the selectable marker chosen. When screening fluorescing cells, the process typically involves exciting cells with light and observing fluorescence from the genes or from molecules made by or associated with the genes in the cells. This visual screening process is slow and not particularly amenable to automation. As a result, the number of cells that can be screened and selected for further processing is greatly limited.

Although electronic cameras have been used to record fluorescence levels from colonies of cells, only the total relative yield of the fluorescence is recorded. This does not distinguish between fluorescence amplitude, which depends on both the photophysical properties of the fluorophore and its concentration, and fluorescence lifetime, which depends only on the photophysical properties of the fluorophore. Thus, directed evolution procedures that rely on steady state measurements of fluorescence select for changes that can be in either the amount of or the chemical properties of the fluorophore, but cannot specifically select for changes in molecular properties independent of concentration.

Also, while the use of electronic cameras has made it possible to screen cells more rapidly, its application has been limited by the ability to manually select cells exhibiting desired traits. What is needed, therefore, is a more sensitive, higher resolution system that quantitates levels of fluorescence from microcolonies (colonies with a diameter of approximately 100 microns or less) or from individual cells, thus allowing cell screening on the order of millions of cells per round of directed evolution, coupled with an automated system for selecting the microcolonies or cells of interest.

Thus, the ability to perform directed evolution using a high resolution fluorescent assay that is sensitive, amenable to automation, and that distinguishes between fluorescence amplitude and fluorescence lifetime would be a significant asset for research as well as diagnostics and therapeutics.

SUMMARY OF THE INVENTION

This invention relates to a method for screening large numbers of individual cells or microcolonies based on fluorescence lifetime of fluorescent markers present in the cells. This invention involves:

providing a substrate with multiple locations, at least some of which contain one or more cells containing a fluorescent marker;

directing a light beam onto each location, thereby causing the fluorescent marker to emit fluorescent light;

automatically detecting the fluorescent light;

automatically measuring and recording the lifetime of the fluorescent light; and correlating the lifetime of the fluorescent light with the location containing the cell with the fluorescent marker emitting the fluorescent light.

This invention further relates to a method for generating a high-resolution image map of cell fluorescence lifetime and using the image map to select cells exhibiting desired fluorescent properties.

This invention further relates to a method for automatically selecting cells exhibiting desired characteristics of imagable properties, such as fluorescence, color, morphology, or any other characteristic that may be detected and recorded, by selectively killing those cells not exhibiting the desired characteristics. In one embodiment, this involves:

providing a substrate with multiple locations, at least some of which contain one or more cells expressing an imagable property;

detecting and recording the imagable property;

identifying and recording locations containing cells expressing a desired characteristic of the imagable property and locations not containing cells expressing the desired characteristic of the imagable property; and scanning lethal irradiation across the substrate through a high speed shutter and through an objective, wherein the shutter is open only when the objective is positioned over locations not containing cells expressing the desired characteristic of the imagable property to thereby kill the cells in such locations.

In an alternative embodiment, the invention involves:

providing a substrate with multiple locations, at least some of which contain one or more cells expressing an imagable property;

detecting and recording the imagable property;

identifying and recording locations containing cells expressing a desired characteristic of the imagable property and locations not containing cells expressing the desired characteristic of the imagable property; and projecting lethal irradiation only onto those locations not containing cells expressing the desired characteristic of the imagable property to thereby selectively kill those cells.

In both cases, light that is not in and of itself lethal can be used in place of lethal radiation if the cells are first treated with a sensitizing agent or are induced to synthesize endogenous sensitizing agents.

This invention further provides for an apparatus for the automated screening and selection of cells based on fluorescence properties.

This invention may be used with both prokaryotic and eukaryotic cells. This invention is useful in directed evolution methodologies but also may be used to screen and select cells in situ.

BRIEF DESCRIPTION OF THE DRAWINGS

FIG. 9 is an illustration of one example of an optically patterned cell growth. FIG. 9A is a drawing of an image projected onto *E. coli* grown in the presence of a cationic porphyrin and plated onto an LB-plate, while FIG. 9B is a photograph of the pattern of cell growth resulting after the plate is exposed to visible light.

DETAILED DESCRIPTION OF THE INVENTION

Figure 1:
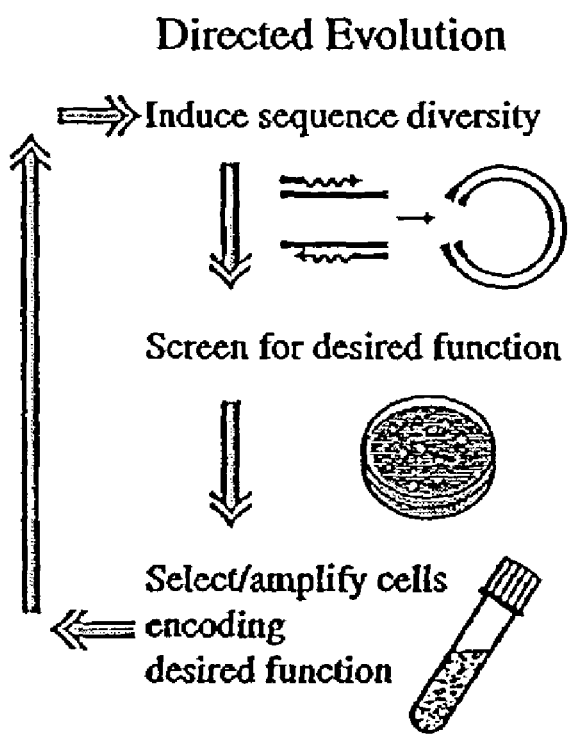
FIG. 1 is a schematic diagram illustrating the general process for directed evolution.

This invention provides a method for screening large numbers of individual cells or colonies of cells using scanning microscopy coupled with fluorescence lifetime measurement and analysis, using time-correlated single photon counting. Both the imaging of the fluorescence lifetime data from cells and/or colonies on a surface and the analysis of this data are controlled and performed in an automated and rapid manner using a computer. This screening method can then be used with either light-mediated patterned cell growth methodologies, as further provided by this invention, or mechanical methods to select individual cells or colonies based on their fluorescent properties.

This invention provides two distinct improvements over current methods for screening cells. First, automated scanning of the fluorescent properties of cells or colonies enables a large number of colonies to be screened rapidly and automatically. In the practice of this invention, a slide containing millions of cells can be examined in minutes. Second, the method allows one to determine independently the lifetime and the amplitude of the fluorescence. Current methods of screening involve either a manual or automated survey of total fluorescence, which depends on both the lifetime and the amplitude of the fluorescence. By distinguishing between lifetime and amplitude, one can determine whether changes in fluorescence are due in changes in numbers of fluorophores or changes in the excited state lifetime (i.e., the chemical properties) of the fluorophores.

The invention further provides an automated method for selecting cells that exhibit desired characteristics. In one embodiment, this method utilizes a computer-controlled scanning microscope system to focus a laser beam onto a surface upon which cells immobilized on the timescale of the procedure. The cells that are illuminated in this way are killed or their growth is inhibited. The focused laser beam is scanned across the surface and turned on and off during the scanning process such that only non-irradiated cells survive, resulting in a patterned growth of cells. Alternatively, other scanning systems, such as acousto-optical scanners, scanning mirror systems, or other scanning systems known in the art can be used.

In an alternative embodiment of this patterned growth cell selection method, a computer-controlled projection device, such as a micro-mirror array or a liquid crystal display system, is used to project an image onto the cells. Cells onto which this image is projected are killed or their growth is inhibited, again resulting in a patterned growth of cells. As used herein, projection can be accomplished by directing a specific image onto a substrate, by providing a mask to thereby cover portions of the substrate not to be irradiated, or by other methods known in the art.

In both embodiments, inhibition of cell growth occurs either by the use of light wavelengths that are themselves lethal to the cells, such as ultraviolet light, or via the use sensitizing chemicals that absorb light at particular wavelengths and generate lethal damage to the cell.

By employing this invention, cells can be selected with high spatial resolution, and large numbers of cells can be processed. Importantly, this cell selection can be done strictly based on function, as manifested in some detectable property of the cell such as fluorescence or absorbance. This is in contrast with other high throughput selection procedures that utilize large numbers of cells, but require that the selected trait confer a significant growth advantage. This process is preferably coupled with high throughput imaging of cell fluorescence using either a sensitive charge couple device based camera (CCD) camera or a scanning microscope.

This invention permits selection of desirable cells in directed evolution techniques, since cells can be selected with great resolution at sub-visual sizes, allowing a vast number of cells to be processed at once, without the need for antibiotic resistance markers or growth on selective media lacking required nutrients. This invention can also be used in color-based assays for transformation of bacterial cells with plasmid DNA, obviating the need for antibiotic resistance. Further, cell patterning can be used with essentially any cell type, including yeast and mammalian cells, using appropriately selected or modified chemical sensitizers.

Spatially Imaged Fluorescence Lifetime Detection Device

The spatially imaged fluorescence lifetime detection device comprises a scanning microscope system with a nanopositioning or micropositioning stage, or a laser scanning system, modified by the inclusion of a pulsed excitation source, a photon counting detector and appropriate time correlation electronics. In one embodiment, a confocal microscope is used, although other microscope systems may also be used. The positioning capability can be in either two or three dimensions, and allows computer controlled movement system that can position the focal point of a beam on a sample with submicron accuracy. Such positioning stages or scanning systems are commercially available from, for example, Mad City Labs (Madison, Wis.; Nanoh100-xy), PI (Physics Instruments, Germany) or Brimrose Corporation of America (Baltimore, Md.). Alternatively, the stage may be kept stationary while the beam is moved relative to the stage.

The pulsed excitation source can be any laser or light source with a high repetition rate and a short pulse width, generating pulses at greater than 10 kHz. In one embodiment, an actively mode-locked NdYAG laser is used, generating pulses at 80 MHz, which, after compression, are 5 ps in duration. The wavelength used to excite the sample varies according to the sample. In another specific embodiment, an ultrafast titanium sapphire oscillator is used, pumped by a continuous laser source such as a diode-pumped NdYAG laser. The oscillator produces pulses of about 100 femtosecond duration at a repetition rate of 80 MHz.

The photon counting device may be any detector capable of detecting and counting photons, generating electrical pulses for each photon detected. In one embodiment, an avalanche photodiode is used. Alternatively, a photomultiplier tube is employed. Such devices are well known in the art.

The time correlation electronics is any device that can receive information both from the photon counting device and from the laser, or from a fast photodiode associated with the laser, and record time in two dimensions. Preferably, the device uses time correlated single photon counting (TCSPC) to determine the time between a laser pulse and the resulting photon emission (i.e., the excited state lifetime of the molecule giving rise to the photon, generally in the nanoseconds time frame) and it records the time at which the photon arrives, in the lab time frame, typically with microsecond to millisecond accuracy. Such time correlation electronics are commercially available from, for example, Becker & Hickl (Berlin, Germany) or PicoQuant (Berlin, Germany).

In the practice of the invention, a beam from the high repetition rate pulsed laser is passed into the microscope, reflected from a dichroic mirror, and used to excite a sample. Preferably, the sample sits on a 3-D translation/positioning stage or the laser position is controlled by a scanning device such as a rotating mirror or an acousto-optic scanner (these devices will be collectively referred to as "positioners") and its position relative to the focused laser beam is controlled by the computer, thus allowing scanning of the sample. The sample consists of single cells or colonies of cells sitting on, or embedded in, a solid substrate so that their positions do not vary over the period of time required to obtain the image. The cells may be either prokaryotic or eukaryotic, with at least some portion of the cells exhibiting fluorescence, or other imagable property, when excited.

Upon excitation, the sample emits a fluorescent signal that passes through various optical elements. In one embodiment, the fluorescence passes through the dichroic mirror, as the fluorescence is at a wavelength that is not reflected by the dichroic mirror. Each photon emitted by the sample is counted at the detector and the time of arrival of each emitted photon relative to the laser pulse is correlated, stored and analyzed on the computer.

Figure 2:
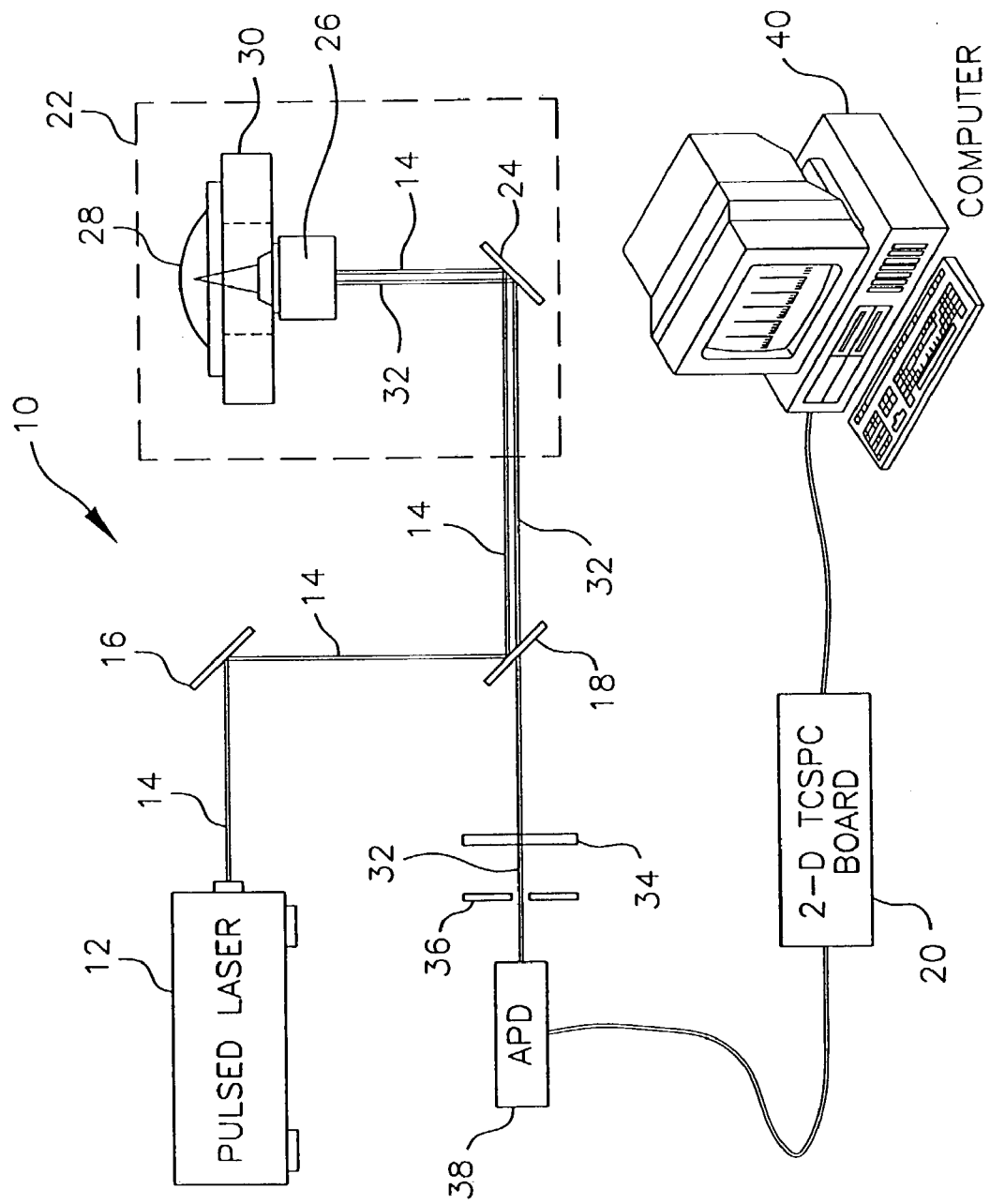
FIG. 2 is a schematic diagram of one embodiment of a fluorescence lifetime imaging system.

FIG. 2 shows one embodiment of the spatially imaged fluorescence lifetime detection system 10. A high frequency (greater than 10 kHz) pulsed laser system 12 is used as the excitation source. The laser emits a light beam 14, which is directed via the use of a mirror 16 to a dichroic mirror 18. The laser is connected to a 2-D TCSPC board 20, which receives an input from the laser that marks the time at which the laser pulse was initiated.

The dichroic mirror 18 reflects the laser light beam 14 into the microscope system 22, where it is directed via additional mirror(s) 24 to the objective lens 26. This lens system focuses the beam onto the sample 28. The sample is attached to a computer-controlled positioning stage 30.

The laser beam excites molecules within at least some of the cells on the stage, causing them to emit light as fluorescence. Some of this fluorescence 32 is captured by the objective lens 26 and passed back into the microscope along the same path through which the laser light beam 14 entered.

The fluorescence is reflected from mirror 24 to the dichroic mirror 18, where the fluorescent light passes through, as the dichroic mirror is selected to reflect light at the wavelength of the laser light beam but transmit light at the wavelength of the fluorescent light. The fluorescent light 32 then passes through a filter 34 to remove any remaining laser light while efficiently passing light in the wavelength region of the fluorescence and, optionally, through a confocal pinhole 36 (typically on the order of 50 to 150 microns in diameter and translatable along the axis of the laser beam) to better define the volume of sample being probed.

The fluorescent light is detected by an avalanche photodiode 38, which generates electrical pulses for each photon of fluorescent light it detects. These pulses are transmitted to the TCSPC board 20. The TCSPC board records the time at which the photon arrived and uses time correlated single photon counting to determine the time between the laser pulse and the photon emission. This information is transmitted to a computer 40, where it is stored and analyzed. Optionally, computer 40 is interfaced with the positioning stage 30.

Figure 3:
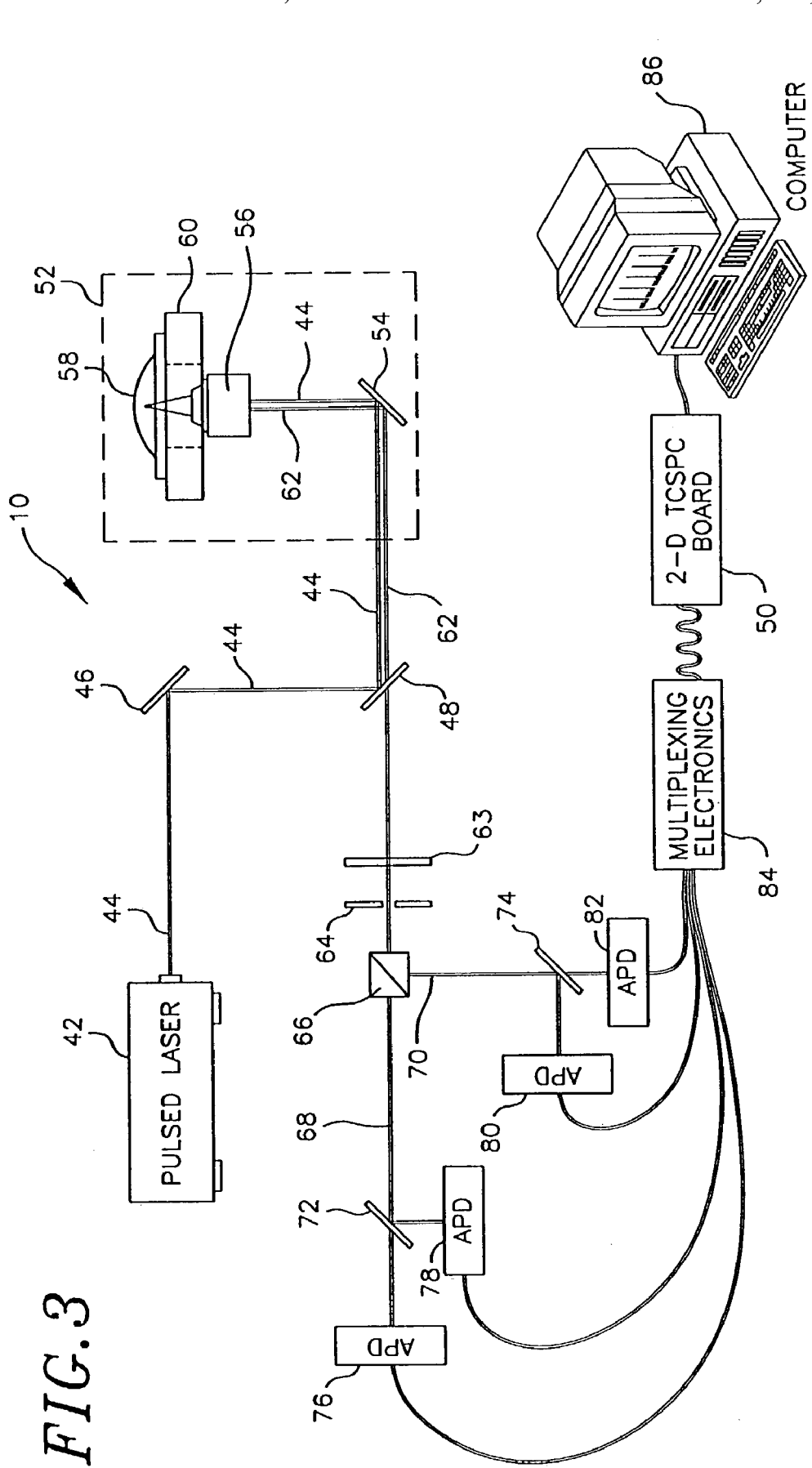
FIG. 3 is a schematic diagram of a four channel fluorescence lifetime imaging system.

An alternative embodiment of the spatially imaged fluorescence lifetime detection device is shown in FIG. 3. In this embodiment, a four channel system records not only the excited state lifetime of each fluorophore that gives rise to each photon detected, but also records the polarization of the photon and wavelength region in which it was emitted. This additional information can also be used to determine which cells or colonies exhibit the most desirable characteristics; for example, those cells containing the most desirable gene products in the directed evolution process.

In this embodiment, the pulsed laser 42 emits a light beam 44, which is directed via the use of a mirror 46 to a dichroic mirror 48. The laser is connected to a 2-D TCSPC board 50, which receives an input from the laser that marks the time at which the laser pulse was initiated.

The dichroic mirror 48 reflects the laser light beam 44 into the microscope system 52, where it is directed via additional mirror(s) 54 to the objective lens 56. This lens system focuses the light beam onto the sample 58. The sample is attached to a 2-D positioning stage 60 controlled by a computer (not shown).

As the laser beam excites molecules within at least some of the cells on the stage, fluorescent light 62 is emitted, some of which is captured by the objective lens 56 and passed back into the microscope along the same path through which the laser light beam 44 entered. Upon reaching the dichroic mirror 48, the fluorescent light passes through the dichroic mirror, through a filter 63 and, optionally, through a confocal pinhole 64.

The fluorescent light then enters a polarizer 66, emerging from the polarizer in two perpendicular planes 68, 70 as polarized light, each of which enters a wavelength separator 72, 74. Polarized light passing through the wavelength separator is again split into two paths of light, each of which is detected by an avalanche photodiode 76, 78, 80, 82. The avalanche photodiode generates electrical pulses for each photon of fluorescent light it detects. These pulses are transmitted through multiplexing electronics 84 to the TCSPC board 50. The multiplexing electronics comprise a circuit which adds a different period of delay time to the pulses arriving from different channels (Becker & Hickl, Berlin, Germany). In this way the TCSPC board is able to differentiate between the signals from the four different detectors. The TCSPC board records the wavelength region and polarization of each photon, in addition to the lifetime of the excited state that gave rise to the photon. These attributes are all be recorded along with the arrival time of each photon in the lab time frame with a millisecond resolution. This information is transmitted to a computer 86, where it is stored and analyzed.

In the embodiments illustrated in FIGS. 2 and 3, a scanning fluorescent microscope is used to image the fluorescence from cells, which is then used to determine which regions of the surface are to be illuminated with lethal irradiation. Various other methods for imaging cells can also be used. For example, a charge couple device based camera (CCD camera) may be used. It is also possible to monitor absorbance in a spatially resolved fashion or to use a scanning probe microscope to generate an image of the morphology, electrical characteristics, surface properties, etc., of cells. Any imaging system with sufficient spatial resolution to resolve the features important in identifying cells with desired properties may be employed.

Light Mediated Patterning in Cell Selection

The lifetime image determined by correlating the excited state lifetime measured by the spatially imaged fluorescence lifetime detection system with the position of the positioner at the time of the measurement within the lab time frame can be used to determine which of the cells or colonies in the sample have the desired characteristics. Then, any of several computer-controlled methods for rapidly selecting individual cells or colonies can be employed to either remove specifically the cells of interest (positive selection) or to kill cells that do not have the desired qualities (negative selection). For example, any of several automated mechanical methods for picking cell colonies and moving them to a clean substrate can be used. Whatever selection method is used, the lifetime image of the cells or colonies is stored on a computer and the computer can be then used to automatically decide which cells should be selected, using this information to initiate an automated procedure for cell selection.

The present invention provides methods for selecting cells based on patterned cell growth. This method employs a negative selection strategy, in which cells identified not to exhibit the desired characteristic are selectively killed using a scanning laser. Alternatively, a light "image" is projected onto the sample that kills the unwanted cells.

In one embodiment, fluorescence from cells on a surface is recorded by a scanning fluorescence microscope capable of recording both the fluorescence amplitude and its lifetime, via the use of single photon counting technology, as described above. The image thus obtained of the fluorescence on the surface is used to determine which cells or colonies exhibit the desired fluorescence characteristics. This information is processed and a new image (the "kill image") is generated by the computer. This kill image is designed to irradiate the undesirable cells (that is, those not exhibiting the desired fluorescence characteristics) under conditions that are lethal to those cells, leaving the cells with desirable fluorescence properties to continue growing. The kill image is projected by scanning a UV laser across the surface of the plate, using a fast shutter (typically an acousto-optic modulator) to determine at what positions lethal irradiation occurs. One UV laser suitable for use in this invention is an argon ion laser.

Figure 4:
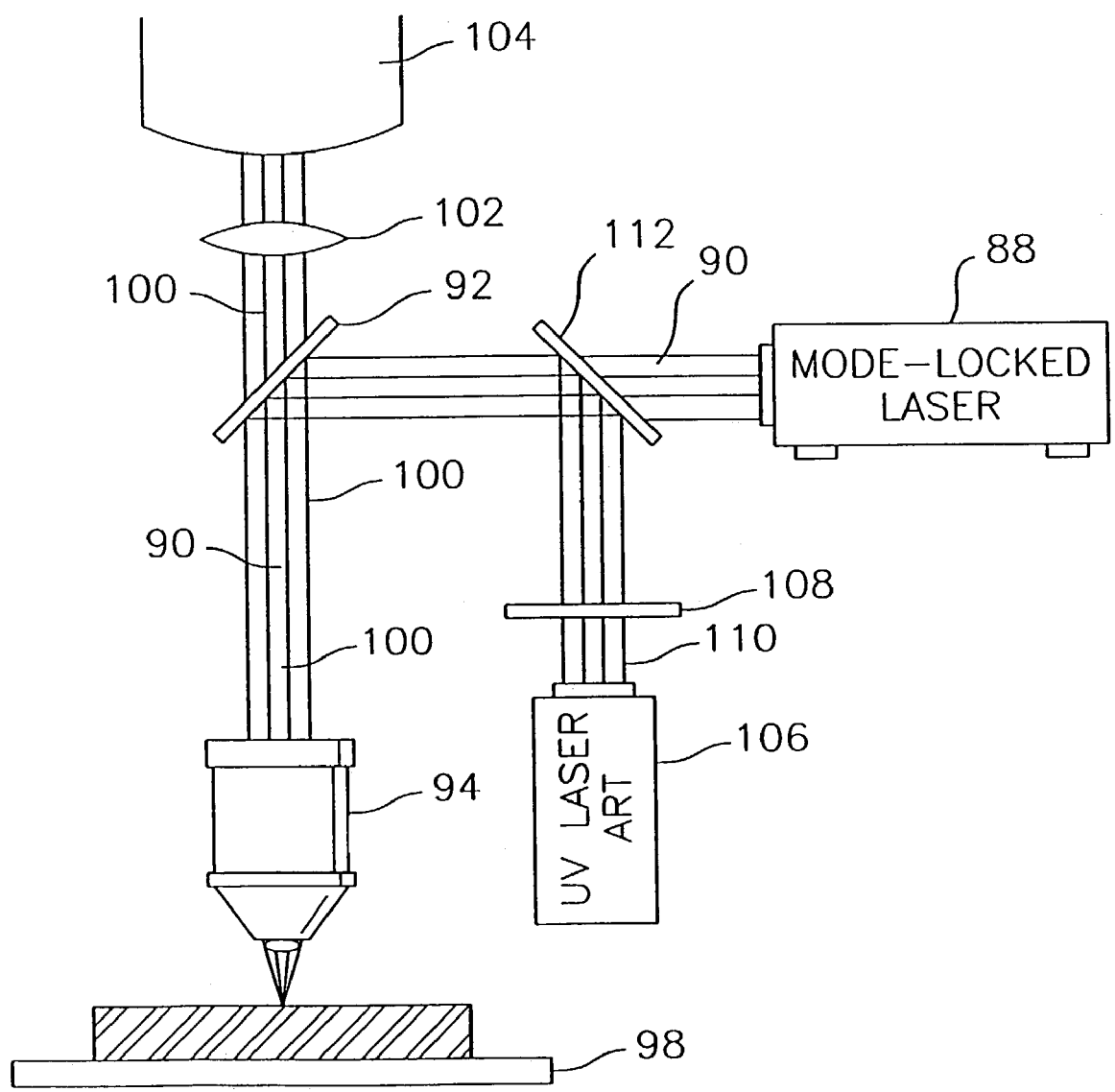
FIG. 4 is a schematic diagram illustrating the use of a confocal microscope with a scanning stage to inspect and evaluate individual cells for fluorescence lifetimes and amplitudes, followed by selective killing of undesirable cells by an intense burst of ultraviolet light from an electro-optically shuttered argon laser.

FIG. 4 shows an example of the use of a UV laser with a scanning fluorescence microscope to select cells based on their fluorescent properties. In FIG. 4, a mode-locked pulsed laser system 88 is used as an excitation source. The laser emits a light beam 90, which is directed to a dichroic mirror 92. The laser is connected to a 2-D TCSPC board (not shown), which receives an input from the laser that marks the time at which the laser pulse was initiated.

The light beam is reflected into a microscope system by the dichroic mirror 92, into the objective lens 94. This lens system focuses the light beam onto a sample of cells located on the surface of a plate 96 positioned on a translation or positioning stage 98, causing some portion of the cells to emit fluorescent light 100. Some of this fluorescence is captured by the objective lens and passed back into the microscope along the same path through which the laser light entered. Upon reaching the dichroic mirror 92, the fluorescence passes through as the dichroic mirror is designed to reflect light at the wavelength of the laser but transmit light at the wavelength of the fluorescence. Optionally, the fluorescence is then passed through a collimating lens 102 and a confocal pinhole (not shown).

The cell fluorescence is imaged by scanning the stage, detecting the fluorescence with a detection system 104, as shown in detail in FIG. 2, and recording both the amplitude and the lifetime of the emission at each point using time correlated single photon counting techniques. The image thus generated is stored and analyzed in a computer (not shown) and used to determine which cells or colonies on the surface should receive lethal irradiation from the UV laser 106. A computer controls both the position of the stage 98 and the shutter 108 in conjunction, such that UV light 110 from the UV laser is directed via mirrors 92, 112 to the sample, specifically irradiating the undesirable cells with UV light, thus killing them. In this figure, mirror 112 is a dichroic mirror that reflects UV light, while transmitting light at the wavelength of the pulsed laser. Other configurations are possible. Importantly, the divergence properties of the UV laser are optimized so that its focal point is in the same position along the axis perpendicular to the sample surface as the longer wavelength measuring beam is.

It is also possible to use a visible laser beam in conjunction with the scanning laser approach to patterning cell growth if the cells are first sensitized to visible light by any of a number of means described below. This has the advantage that the same laser that is used to monitor the fluorescence from the cells can be used to kill the cells simply by increasing the light intensity to a lethal level.

It is also possible to use an ultrafast laser pulse (on the order of a few hundred femtosecond duration) as both the excitation source for performing the time correlated single photon counting measurements of excited state lifetimes and as the source of light to directly kill the unwanted cells even without the use of sensitizers. Both processes can be performed by multiphoton excitation. The very high peak intensity of short pulses make it possible for the fluorophore, such as GFP, to absorb two photons of near infrared light and then to fluoresce in the usual visible region.

This has several advantages. First, since the excitation is in the near infrared, it is very well separated spectrally from the fluorescence. This decreases the background due to scattering of various kinds as well as other fluorescent materials. Second, because the process depends on multiple photons, the volume of material where the photon density is high enough to cause the multiphoton absorption is smaller, increasing the spatial resolution of the technique. Finally, by using near infrared or even infrared light as the source of photons for the multiphoton excitation, it is possible to excite fluorophore in cells below of surface of a sample allowing three dimensional mapping of the fluorescence, as long wavelength light will penetrate more deeply than visible or UV light. This deep probing occurs without exciting fluorophore in the cells above, because the intensity of light will only be great enough as the focal point of the beam to perform the multiphoton excitation.

The same procedure can be used to kill cells by producing the same transitions in DNA and protein molecules that make UV light absorption lethal, by using multiple photons of longer wavelength light. This can be done effectively by simply increasing the intensity of the laser beam when focused on the cell or cells to be killed. Multiple photons will then excite the same transitions in DNA and protein that UV light does and kill the cells. The great advantage here is that a single beam of light can be used both to probe and to kill the cells. As noted above for multiphoton excitation of fluorescence, multiphoton excitation of bactericidal transitions in DNA and protein molecules in the cell can be performed with higher spatial resolution that can be done with UV light. In addition, the near infrared or infrared laser pulses can penetrate the surface allowing for three dimensional killing of cells. Because the unfocused light does not have the intensity to cause multiphoton excitation of lethal transitions, the killing will only occur at the focal point of the laser and not in the cells above.

The intensity and wavelength of the laser beam used for multiphoton excitation screening and cell selection depends both on the specific fluorophores being used and on the geometric constraints of the sample. The wavelength used for screening need be a multiple of the absorbance wavelength preferred for the fluorophore to be excited. The power level of the laser is also dependent on the nature of the fluorophore, the concentration of the fluorophore and the size of the region to be excited at any given time. Generally, the minimum laser intensity required to obtain a substantial signal from the fluorophore should be used, and this can be determined by performing test scans with increasing light levels. For killing cells in particular patterns, the wavelength and intensity depends on the mechanism of killing employed. For example, if a specific sensitizer is used, the wavelength of the laser need be a multiple of the absorbance wavelength of the sensitizer. The appropriate power again be determined by increasing the laser in test scans until cell death is regularly achieved. If no sensitizer is used, multiphoton excitation of DNA and/or protein molecules in the cell are possible by picking an excitation wavelength that is a multiple of a wavelength in the absorbance range of these molecules (190–290 nm). The intensity required will depend on the multiphoton absorption cross section and the cell type. Again this can be determined empirically by increasing the intensity in a test case until high resolution cell death is achieved. Multiphoton beams have previously been used for "nanosurgery" at the subcellular level (Konig, 2000, J. of Microscopy, vol. 200, 83–104).

In an alternative method of light mediated patterning in cell selection, fluorescence from cells on a surface is recorded by a CCD camera. The image of the fluorescence on the surface is used to determine which cells or colonies contain the desired fluorescence characteristics (i.e., which cells are expressing biomolecules that have the desired traits). This information is processed and a kill image is generated by the computer. This image is designed to irradiate the cells that are undesirable under conditions which will prove lethal to those cells and leave the cells with desirable fluorescence properties to continue growing. In one embodiment, the kill image is the inverse of the fluorescence image. Thus, when the kill image is projected onto the cells, the cells with the highest fluorescence receive the least radiation (and thus continue growing) while cells with the lowest fluorescence receive the greatest dose of radiation (and are thus killed). Alternatively, the new image can be designed to irradiate all cells with fluorescent activity below a predetermined threshold. Other kill image configurations are apparent.

The kill image is projected using a computer-controlled imaging system such as micro-mirror array chips (digital light processors or DLPs) or liquid crystal projection units that are commonly used for projecting computer generated images on screens (available from Texas Instruments, Dallas, Tex. or InFocus Corporation, Wilsonville, Oreg.). These projection systems must be significantly modified for this purpose. The lamp is selected to emit light at a wavelength or range of wavelengths suitable for killing selected cells. Also, the imaging optics must be selected both to be appropriate for the size of the image to be generated and for the wavelength region of light used. Finally, appropriate filters must be used to select the desired wavelength regions of light. In particular, a high quality lens system with low optical aberrations is used such that the inherent resolution of the instrument is maintained when the image is reduced to the size of the target.

In one embodiment, the computer storing the kill image is connected to an InFocus® model projector, which uses the video output from a computer to display an image onto a screen (InFocus Corporation, Wilsonville, Oreg.). The focal optics of the projector are replaced by a 50 mm Nikon® lens area, so that the output can be focused on the cells with image features having the proper size and alignment (Nikon, Inc., New York, N.Y.). Other lens systems can also be used, depending on the size of the target area. The projector uses an aluminum micro-mirror array that is electronically controlled. Suitable chip dimensions are 1024×786 pixels, although other dimensions may be used depending on the desired resolution. When focused on an agar plate containing cells, the image size is approximately 11 cm by 8.5 cm, producing a pixel size of approximately 0.07 mm/pixel. Such an optical arrangement allows selective imaging and killing in a library of 100 micron colonies containing several hundred thousand members.

Figure 5:
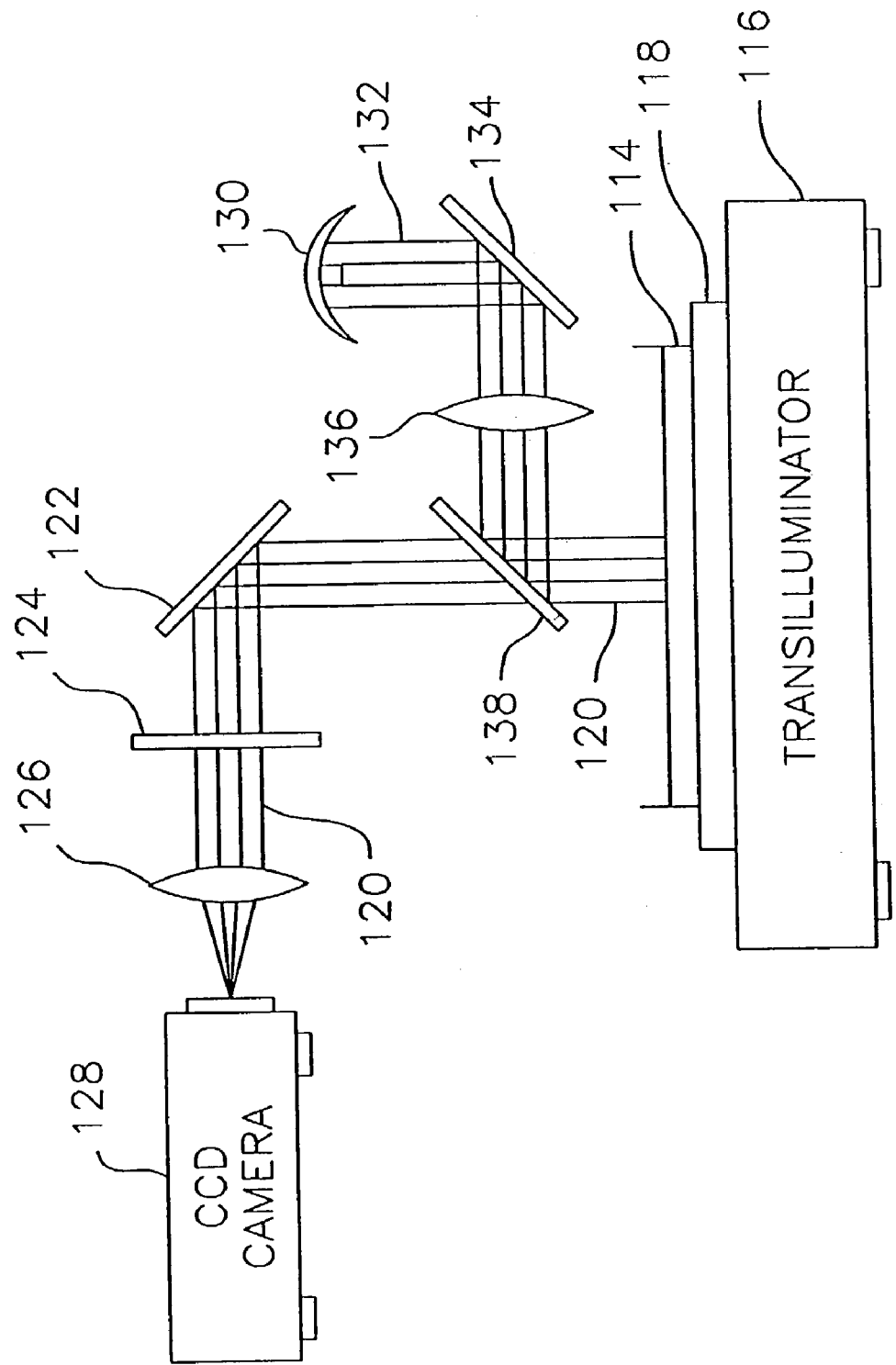
FIG. 5 is a schematic diagram illustrating the use of a CCD camera to screen for fluorescence from cells and a digital light processor to specifically irradiate cells with ultraviolet light to kill individual cells that do not exhibit desired characteristics.

FIG. 5 shows a CCD camera being used to image the fluorescence from cells. This information is then used by the computer to generate the kill image of lethal irradiation projected onto the plate of bacteria. In this embodiment, the cells to be screened and selected are grown in a plate 114 on agar or other solid substrate, preferably which supports growth of the cells. The plate is supported on a transilluminator 116, with a filter 118 between the plate and the transilluminator. The filter 118 is selected to permit a wavelength or wavelengths of light suitable for exciting fluorescence of the cells to pass from the transilluminator 116 to the cells on the plate 114, but not wavelengths that would interfere with the detection of fluorescence from the cells.

Fluorescence 120 emitted from the excited cells is reflected from a mirror 122, through a filter 124 and a lens 126 into a CCD camera 128. The fluorescence image detected by the CCD camera is stored in a computer (not shown) and is used to generate the kill image designed to selectively kill cells not exhibiting the desired traits. An ultraviolet light source 130 emits UV light 132 into a digital light processor 134, which projects the UV light image through a lens 136 and onto a dichroic mirror 138, selected to allow the fluorescence used for imaging by the CCD camera to pass through and UV light to be reflected. The dichroic mirror 138 reflects the UV light image onto the cells in the plate 114, selectively killing some portion of the cells.

Various other methods for imaging cells could also be used. Alternatively, one could use a scanning fluorescence microscope (one example is a scanning microscope capable of determining the lifetime of the fluorescence, its polarization and its wavelength region, as is discussed above with reference to FIG. 3). It is also possible to monitor absorbance in a spatially resolved fashion or to use a scanning probe microscope to generate an image of the morphology, electrical characteristics, surface properties, etc. of cells. Any imaging system that works with high enough spatial resolution to resolve the features important in determining which cells have the most advantageous properties for the directed evolution project of interest would work.

Both of the above embodiments of a system for automated cell selection use UV light as the source of lethal irradiation. The use of UV light is both a simple and an efficient means to kill cells. However, alternative methods using visible or near infrared light sources are also available. When using visible or near infrared light, a sensitizing agent is first applied to the cells that will absorb the light, using the light energy to either directly damage the cell or to generate a chemical species that damages the cells. Alternatively, cells may be chemically induced to produce endogenous photosensitizers.

One example of a sensitizing agent is an intercalating or DNA binding dye, such as ethidium bromide, thiazole orange, etc. These dyes associate directly with DNA and, upon light absorption, can cut or damage the cell DNA, causing cell death. Alternatively, singlet oxygen generating molecules, such as porphyrins, certain cyanine dyes and the like may be used. In their excited state, these molecules can interact with molecular oxygen (normally in a triplet form) to generate the highly reactive singlet oxygen species. Singlet oxygen reacts with most organic compounds, often destroying their normal function in the process. If enough damage is done, the cell dies.

Porphyrins are strong absorbers of visible light, and many form long lived triplet states upon excitation with visible light. Since the amount of damage done to the cells depends on the amount of light absorbed by porphyrins in the cell, which, in turn, is a function of the amount of porphyrin in the cell and the amount of incident light, cells in relatively dark areas have a much higher chance of survival than cells in relatively bright areas of the image. The more porphyrin there is in a cell, and the more light incident on that area of the plate, the more damage will be done, and thus the chance of cell survival will be less.

For gram-negative bacteria, cationic porphyrins have been found to be the most efficient exogenous porphyrin photosensitizers. Chemical sensitizers for a large variety of cell types, including eukaryotic cells, are well known in the art. For example, several chemical photosensitizers are described in the photodynamic therapy literature, in which chemicals that are taken up more rapidly by cancer cells or by pathogens relative to normal cells are used to sensitize these cells to destruction by light.

Two chemical sensitizers effective for use with *E. coli*, a gram negative bacteria, are tetra(4N-methylpyridyl) porphine and tetra(4N, N,N-trimethyl-anilinium) porphine. Greater than 99.99% of *E. coli* cells are killed by incubation with these porphyrins at 10 ug/mL for 5 minutes, followed by irradiation at 6 mW/cm$^2$ for 20 minutes. By contrast, the anionic porphyrin tetra (4-sulphonatophenyl) porphine shows no photoinactivation under the same conditions. Merchat et al. (1996) *Journal of Photochemistry and Photobiology B: Biology* 32: 153–157.

Alternatively, *E. coli* can be induced to synthesize endogenous porphyrins precursors by incubating the cells with d-aminolaevulinic acid at 5–9 mM for 15 minutes. Szocs, et al. (1999) *Journal of Photochemistry and Photobiology B:*

*Biology* 50: 8–17. Following induction, 99.4% inactivation of *E. coli* is seen after 90 minutes of irradiation at 0.08 W/cm$^2$.

Figure 6:
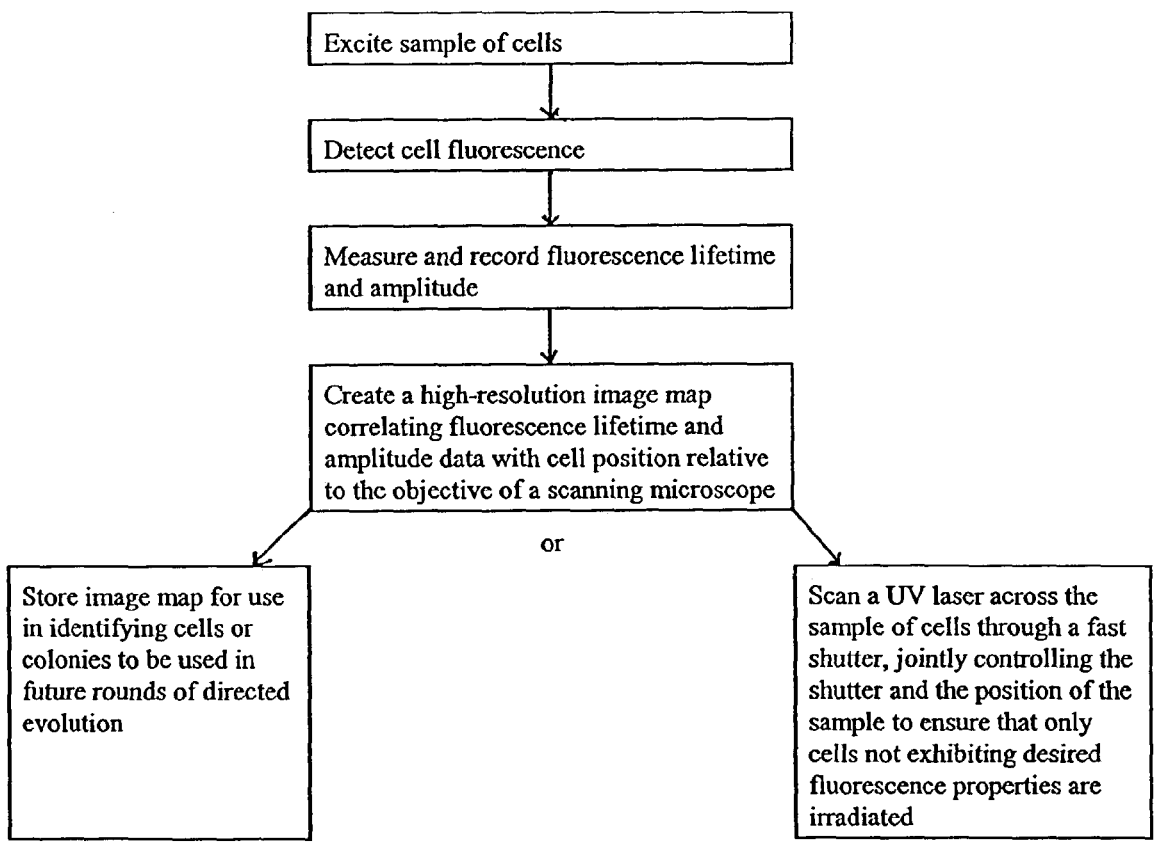
FIG. 6 is a flowchart summarizing the use of the computer interfaced scanning fluorescence microscope in directed evolution methodologies.

Use of Computer Interfaced Scanning Fluorescence Microscope in Cell Screening and Selection in Directed Evolution Methodologies As is apparent from the above discussion, the computer interfaced scanning fluorescence microscope is useful in directed evolution methodologies where fluorescence, or other imagable characteristic, is used as an indicator of protein function to screen and select cells for desired functional characteristics. An overview of this method is shown in FIG. 6.

First, the sample of the cells to be screened is placed on a positioning stage and positioned under the objective of the computer-interfaced scanning microscope. The computer moves the positioning stage, recording the position of the stage relative to the objective in lab frame. At the same time, the cells are excited by a light source, such as a mode-locked laser, through the objective of the scanning microscope. Some portion of the resulting cell fluorescence passes through the objective and is directed to an avalanche photodiode or photomultiplier tube, interfaced with a 2-D TCSPC board and a computer, where the fluorescence lifetime and amplitude and is measured and recorded. The computer is also interfaced with the laser or other light source and records and stores the time at which each laser pulse is initiated.

The fluorescence data is correlated with the position of the positioning stage (and thus the position of the sample), generating a high-resolution image map of individual cell (or microcolony) positions based on the fluorescence lifetime and amplitude data.

This high-resolution map image is stored for use in identifying individual cells or microcolonies expressing desirable functional traits, as measured by fluorescence lifetime and amplitude. These cells or microcolonies are then selected for future rounds of directed evolution.

Alternatively, the high-resolution map is used to generate a high-resolution kill image map of cells or colonies not expressing desirable functional traits, as measured by fluorescence data. Using this kill image map, a UV laser is directed through a fast shutter and into the objective of the scanning microscope, where it is scanned across the sample of cells. Both the shutter and the nanopositioning stage are controlled by the computer such that the shutter is open when undesirable cells or microcolonies are positioned under the objective, killing those cells, while the shutter is closed when desirable cells or microcolonies are positioned under the objective.

As is apparent, this method selectively and automatically kills undesirable cells (or microcolonies) one cell (or microcolony) at a time, greatly increasing the number of cells which can be screened and selected during directed evolution.

Figure 7:
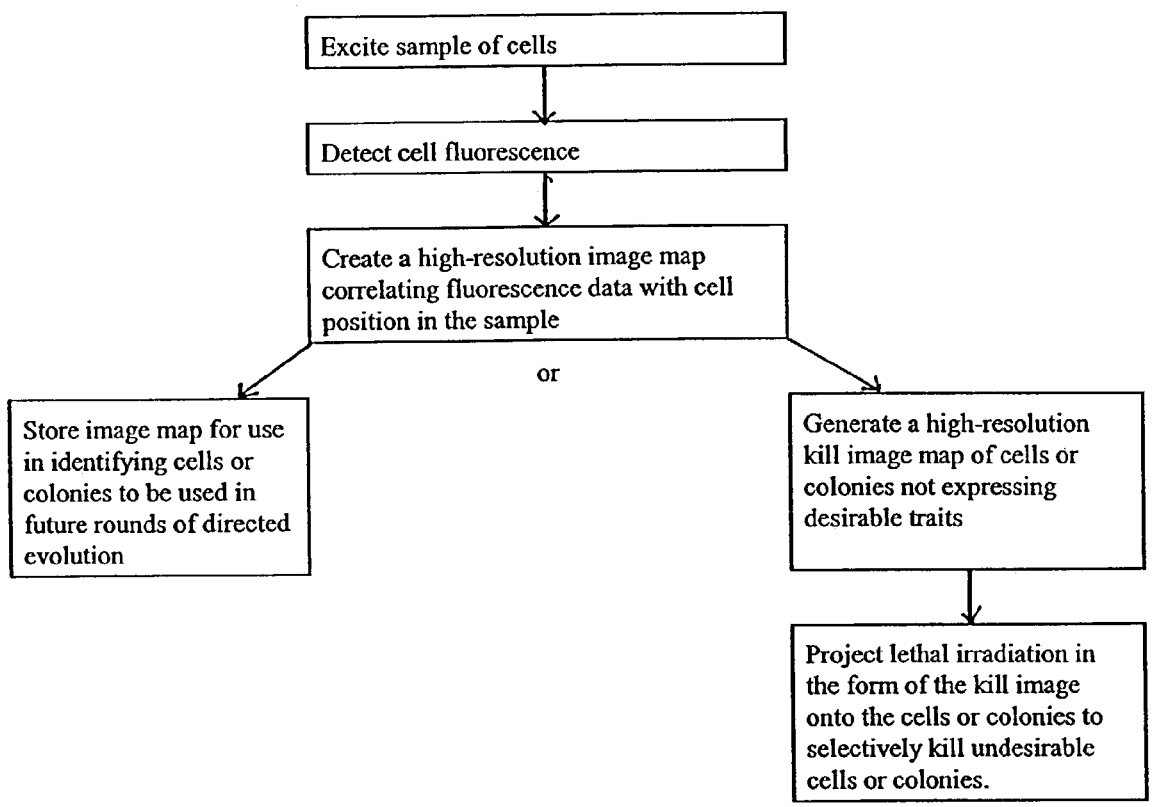
FIG. 7 is a flowchart summarizing the use of light mediated patterning in cell selection using imaging of lethal irradiation in directed evolution methodologies.

Use of Light Mediated Patterning Using Imaging of Lethal Irradiation in Directed Evolution Methodologies FIG. 7 shows an overview of the use of light mediated patterning using imaging of lethal irradiation in directed evolution methodologies where fluorescence, or other imagable characteristic, is used as an indicator of protein function, cell morphology or activity of cellular components. In this method, a high resolution kill map is projected onto a sample, selectively killing large populations of undesirable cells while permitting desirable cells to continue growing.

First, a sample of cells to be screened for fluorescence is excited by a light source such as a transilluminator, causing some portion of the cells to fluoresce. This fluorescence is detected and recorded by an electronic camera, such as a CCD camera, interfaced with a computer. The fluorescence data is used to create a high-resolution map correlating fluorescence with cell (or microcolony) position within the sample.

Next, the fluorescence image is used to generate a high-resolution kill map of cells (or microcolonies) not expressing desirable functional characteristics. Lethal irradiation, such as UV light, is projected onto the sample in the form of the kill image. Alternatively, the sample is first treated with a photosensitizer, or endogenous photosensitizers are induced, and a wavelength of light absorbed by the photosensitizer is projected onto the cells in the form of the kill image. The projection of the kill image may be controlled by a digital light processor interfaced with the computer storing the kill image. In any case, the irradiation selectively kills the cells on which the kill image falls, leaving the nonirradiated cells to continue growing.

Because the kill image is a high resolution map based on fluorescence data correlated to desirable functional characteristics, this method of light mediated patterning is a rapid and efficient way to simultaneously select large numbers of cells or microcolonies for further directed evolution studies.

As is apparent, the detection technique used to generate the high resolution map may by varied depending on the imagable property of interest. So long as the property of interest, whether it is cell morphology, calorimetric reactions or the like, can be imaged, a high resolution map can be generated for use in patterned cell selection as described for fluorescing cells.

The cell screening and selection methods described above are not limited to use with bacterial cells. The methodologies of this invention have potential applications for eukaryotic cells as well. For example, patterned cell selection can be used for the selection of yeast cells, which are often used in various techniques in which libraries of gene sequences are generated and specific colonies are selected. Patterned cell selection could also be used in the selection of mammalian cells for similar reasons.

In addition, patterned cell selection could have direct application in the field of photodynamic therapy presently used for treatment of certain types of cancer. Porphyrins selectively accumulate in certain types of cancer cells, causing the cancer cells to fluoresce. Presently, light is used to illuminate all cells in the vicinity of the cancer cells. The cancer cells, due to their higher concentration of porphyrin, are killed faster than the normal cells, but many normal cells die as well.

By using the fluorescence from the porphyrin or from a specific binding fluorophore in the cancer cells to map the growth of the cancer cells on a two dimensional surface, such as the skin, lining of the gut, surface of an organ, etc., and selectively illuminating only the cancer cells, and not the healthy cells, much more complete killing of the cancer could be achieved without harming the healthy cells.

Moreover, because multiphoton excitation permits deep probing and scanning of the cells in three dimensions, it has important implications for medical treatments where it is desirable to specifically target and kill some cells while leaving others intact beyond a two dimensional surface. For example, the multiphoton excitation technique can be used to first screen tumor sites in a patient, using a three dimensional laser scanning methodology (Konig, Journal of Microscopy, Vol. 200, part 2, November 2000, pp. 83–104, hereby incorporated by reference in its entirety). It can then be used to kill selectively cancer cells while leaving non-cancer cells intact. Similarly, many types of benign skin disorders or cosmetic manipulations, such as the removal of hair cells, could be treated using multiphoton excitation screening and selection.

EXAMPLE 1

Figure 8:
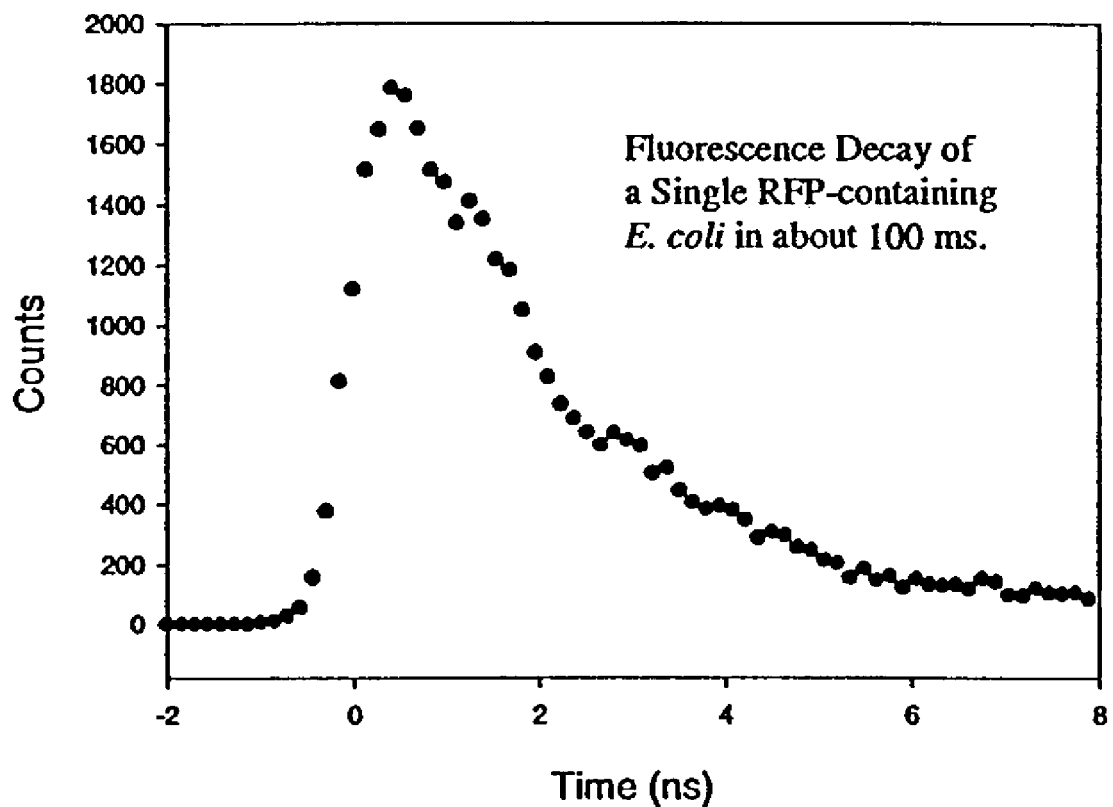
FIG. 8 is a graph illustrating time-correlated fluorescent signals from an individual *E. coli* cell expressing red fluorescent protein.

Time Correlated Fluorescent Signals from Individual *E. coli* Expressing Red Fluorescent Protein FIG. 8 shows time correlated data taken on a single cell of *E. coli* expressing red fluorescent protein (RFP) from the dsRED plasmid, available commercially from ClonTech Laboratories, Inc. (Palo Alto, Calif.). The trace was taken using an apparatus similar to the one shown in FIG. 2, but using a sample suspended in solution rather than on a solid substrate.

Specifically, a frequency doubled, pulse compressed, and mode locked Nd:YAG laser (532 nm, 10 psec) was used to excite the sample at a repetition rate of 82 MHz. To ensure proper beam quality and polarization, the light was passed through a single mode, polarization preserving glass fiber (F-SPA, Newport, Irvine, Calif.) and a polarizing beam splitter (05BC15PH.3, Newport, Irvine, Calif.). The laser light was delivered into an inverted, confocal microscope and reflected up towards the microscope objective with a dichroic mirror (Q570LP, Omega Optical, Brattleboro, Vt.).

The sample, a 50 microliter droplet containing *E. coli* cells expressing the plasmid dsRED to produce red fluorescent protein, was spread onto a glass cover slip (22×50 mm No 1.5, VWR, West Chester, Pa.). The same objective (100×PlanApo 1.4NA, Olympus, Tokyo Japan) used to focus the laser also collected the fluorescence.

The collected fluorescence passed through the dichroic mirror and was focused onto a 50 micron diameter pinhole (910PH50, Newport, Irvine, Calif.). The fluorescence was then split by a polarizing beam splitter (05FC16PB.3, Newport, Irvine, Calif.), sending photons polarized parallel to the laser to detector one and photons polarized perpendicular to the laser to detector two (Perkin Elmer, SPCM-AQR-12, Canada).

To remove Raleigh and Raman scattering, the fluorescence was passed through a custom emission filter (Omega Optical, Brattleboro, Vt.). The filter specifically blocks 532 nm light and the water Raman scattering from 532 nm light. The signal from the detectors and a synchronization signal from each laser pulse were sent into an in-house designed and built signal multiplexor/router. The multiplexor sends a start signal and a stop signal into the Timeharp TCSCP board (PicoQuant, Berlin, Germany). The multiplexor also separates the signals from multiple detectors in regions of time defined by the repetition rate of the laser. Each detector's signal occupies a 12 ns region of time.

The resulting time-correlated fluorescent signals from an individual *E. coli* expressing RFP are shown in FIG. 8.

EXAMPLE 2

Light-Mediated Patterning in Cell Selection

The cationic porphyrin 5,10,15,20-Tetrakis [4-(trimethylammonio)phenyl]-21H,23H-porphine (TmaP), which has a maximum absorption at 412 nm wavelength, was added to a 3 mL liquid culture of *E. coli* in Luria Broth (LB) and the culture was incubated in the dark overnight. Approximately 50 uL of the culture was plated on an LB/TmaP agar plate, and portions of the plate was irradiated for about 2 minutes with visible light passed through a blue filter. The cells were then placed in an incubator and allowed to grow overnight at 37° C.

The image projected onto the plate is shown in FIG. 9A. As shown in FIG. 9B, those portions of the plate receiving visible light (the "white" portion of the image shown in FIG. 9A) show little or no growth. of *E. coli*, while portions of the plate receiving little or no visible light (the "black" portion of the image shown in FIG. 9A) show high density growth in the form of the Arizona State University mascot, the Sun Devil "Sparky."

It is emphasized at this point that the present invention is not intended to be limited to the exemplary embodiments shown and described above. The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Morever, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An automated method for screening and selecting cells, the method comprising the steps of:
   providing a substrate with multiple locations;
   immobilizing a plurality of cells exhibiting an imagable property when excited, either onto or within said substrate;
   detecting the imagable property by scanning a first light beam across the substrate to excite the imagable property of the cells;
   recording the imagable property;
   determining an excited state lifetime of the imagable property for each of the cells;
   identifying and recording locations containing cells expressing a desired characteristic and locations not containing cells expressing the desired characteristic, based on the excited state lifetimes of the cells;
   generating a kill image from the excited state lifetimes and the locations of the cells;
   applying a sensitizing agent to the substrate, wherein the sensitizing agent is selected to render the cells sensitive to light at a particular sensitizing wavelength; and
   scanning a second light beam, according to the kill image, having a wavelength that is a multiple of the sensitizing wavelength across the substrate through a high speed shutter, wherein the shutter is open only when the light beam is positioned over locations not containing cells expressing the desired characteristic of the imagable property to thereby kill the cells in such locations.

2. The method of claim 1 wherein the sensitizing agent is a DNA intercalating dye.

3. The method of claim 2 wherein the DNA intercalating dye is ethidium bromide.

4. The method of claim 1 wherein the sensitizing agent is a porphyrin.

5. The method of claim 1 wherein the sensitizing agent generates reactive oxygen species upon absorption of light.

6. An automated method for screening and selecting cells, the method comprising the steps of:

provicing a substrate with multiple locations;

immobilizing a plurality of cells exhibiting an imagable property when excited, either onto or within said substrate;

detecting the imagable property by scanning a light beam across the substrate to excite the imagable property of the cells;

recording the imagable property;

determining an excited state lifetime of the imagable property for each of the cells;

identifying and recording locations containing cells expressing a desired characteristic and locations not containing cells expressing the desired characteristic, based on the excited state lifetimes of the cells;

generating a kill image from the excited state lifetimes and the locations of the cells;

applying a sensitizing agent to the substrate, wherein the sensitizing agent is selected to render the cells sensitive to light at a particular sensitizing wavelength; and projecting light, according to the kill image, having a wavelength that is a multiple of the sensitizing wavelength only onto those locations not containing cells expressing the desired characteristic of the imagable property to thereby selectively kill those cells.

7. The method of claim 6 wherein the sensitizing agent is a DNA intercalating dye.

8. The method of claim 7, wherein the DNA intercalating dye is ethidium bromide.

9. The method of claim 6 wherein the sensitizing agent is a porphyrin.

10. The method of claim 6 wherein the sensitizing agent generates a reactive oxygen species upon absorption of light.

11. The method of claim 6, wherein the imagable property of the cells is sensed and recorded by a charge couple device based (CCD) camera.

12. The method of claim 6, wherein a computer-controlled projection device is used to project the light onto the cells not exhibiting the desired characteristic of the imagable property.

13. The method of claim 6, wherein the computer-controlled projection device is a digital light processor.

14. The method of claim 1 wherein the first and second light beam are produced by the same light source.

* * * * *